United States Patent
Huy et al.

(10) Patent No.: US 10,271,934 B2
(45) Date of Patent: Apr. 30, 2019

(54) TOOTHBRUSH

(75) Inventors: Gerhart P. Huy, Hamilton Square, NJ (US); Vivek M. Patel, Ewing, NJ (US); Christopher B. King, Hampton, NJ (US); Abdul Rahman Kadir, North Point (HK); William James Babbs, Stanley (HK)

(73) Assignee: Church & Dwight Co., Inc., Princeton, NJ (US)

( * ) Notice: Subject to any disclaimer, the term of this patent is extended or adjusted under 35 U.S.C. 154(b) by 144 days.

(21) Appl. No.: 13/098,505

(22) Filed: May 2, 2011

(65) Prior Publication Data

US 2012/0137454 A1 Jun. 7, 2012

Related U.S. Application Data

(60) Provisional application No. 61/419,634, filed on Dec. 3, 2010.

(51) Int. Cl.
*A61C 17/34* (2006.01)
*A46B 15/00* (2006.01)

(52) U.S. Cl.
CPC ...... *A61C 17/3481* (2013.01); *A46B 15/0008* (2013.01); *A46B 15/0044* (2013.01)

(58) Field of Classification Search
CPC ....... A46B 9/04; A46B 15/00; A46B 15/0008; A46B 15/0044; A46B 2200/1066; A61C 17/3481
USPC .................................................. 15/22.1, 105
See application file for complete search history.

(56) References Cited

U.S. PATENT DOCUMENTS

| | | |
|---|---|---|
| 5,160,194 A | 11/1992 | Feldman |
| 5,421,726 A | 6/1995 | Okada |
| 5,544,382 A | 8/1996 | Giuliani et al. |
| 5,590,434 A | 1/1997 | Imai |
| 5,651,157 A | 7/1997 | Hahn |
| 5,930,858 A | 8/1999 | Jung |
| 5,943,723 A | 8/1999 | Hilfinger et al. |
| 6,029,304 A | 2/2000 | Hulke et al. |
| RE36,699 E | 5/2000 | Murayama |
| 6,202,242 B1 * | 3/2001 | Salmon .................... A46B 5/00 15/105 |
| 6,421,865 B1 | 7/2002 | McDougall |
| 6,421,866 B1 | 7/2002 | McDougall |
| 6,606,755 B1 | 8/2003 | Robinson et al. |

(Continued)

FOREIGN PATENT DOCUMENTS

WO  WO 2009136918 A1 * 11/2009 ............. A46B 15/00

*Primary Examiner* — Stephanie R Berry
(74) *Attorney, Agent, or Firm* — Church & Dwight Co., Inc.

(57) ABSTRACT

A toothbrush provides a head with bristles, a neck and a handle. An eccentrically rotational weight is engaged for rotation with a motor. The motor and weight are disposed within the handle. The handle, neck and head each have a different intensity of vibration. The toothbrush houses an electrical circuit, which includes a processor and at least two LEDs (light emitting diodes) at least one of which illuminates the neck and optionally also the head and the ends of the bristles attached to the head. At least two of the LEDs in the circuit are capable of emitting different colored light with respect to each other. The at least two LEDs are switched on for a predetermined time in a predetermined sequence under the control of the processor.

14 Claims, 4 Drawing Sheets

(56) References Cited

U.S. PATENT DOCUMENTS

| | | |
|---|---|---|
| 6,766,548 B1 | 7/2004 | Lukas et al. |
| 6,802,097 B2 | 10/2004 | Hafliger et al. |
| 6,920,659 B2 | 7/2005 | Cacka et al. |
| 6,954,961 B2 * | 10/2005 | Ferber .................... A61C 17/22 |
| | | 15/105 |
| 7,003,839 B2 | 2/2006 | Hafliger et al. |
| 7,240,390 B2 | 7/2007 | Pfenniger et al. |
| 7,254,858 B2 | 8/2007 | Hafliger et al. |
| 7,261,851 B2 | 8/2007 | Hafliger et al. |
| 7,409,741 B2 | 8/2008 | Dworzan |
| 7,418,759 B2 | 9/2008 | Huber et al. |
| 7,441,336 B2 | 10/2008 | Hawes et al. |
| 7,556,320 B2 | 7/2009 | Hafliger et al. |
| 7,574,765 B2 | 8/2009 | Huber et al. |
| 2004/0052076 A1 | 3/2004 | Mueller |
| 2004/0205914 A1 * | 10/2004 | Holden .................. A46B 13/02 |
| | | 15/22.1 |
| 2005/0053895 A1 * | 3/2005 | Pinyayev et al. ................ 433/29 |
| 2008/0196185 A1 * | 8/2008 | Gatzemeyer ....... A46B 15/0002 |
| | | 15/23 |
| 2009/0083918 A1 * | 4/2009 | Taggart et al. ................ 15/22.1 |
| 2010/0050357 A1 * | 3/2010 | Misner ............... A46B 15/0002 |
| | | 15/167.1 |
| 2011/0162155 A1 | 7/2011 | Wai |

* cited by examiner

TOOTHBRUSH

FIELD OF THE INVENTION

This invention relates to hand held appliances, and more especially hand held electrically powered toothbrushes with novel light effects.

BACKGROUND OF THE INVENTION

Children and adults can find the task of brushing their teeth confusing. For example, a person can find it hard to judge how long to brush each section of their teeth. A child could be told to spend two minutes brushing their teeth and spend the two minutes brushing only one or two quadrants of their teeth, which may lead to increased chances of tooth decay where the child has spent an inadequate amount of time brushing their teeth. In addition, a child might find teeth brushing odious and unexciting to the extent that they find it hard to get into the habit of regular teeth brushing. There is a need for improved devices to help children and adults establish regular teeth brushing.

It is well known that plaque and bacteria adhering to teeth make the teeth more susceptible to tooth decay. Dentists generally recommend that toothbrush users brush their teeth for at least two minutes to adequately remove the plaque. However, many toothbrush users do not pay close attention to the brushing time duration to ensure that they have brushed for the recommended brushing time interval (e.g., approximately two minutes). Accordingly, visually signaling users at the start and the end of the recommended brushing time interval would allow them to brush for the desired amount of time without having to monitor the time using a watch or a clock. Further, since many users would brush for the recommended time if they were aware of the starting and ending time, additional plaque would be removed as compared with variable brushing time durations.

Known toothbrushes have utilized a light source to indicate when the recommended brushing time interval has started and ended. However, the known toothbrushes utilize light sources that do not illuminate the neck of the toothbrush. Accordingly, a user brushing their teeth may not see the light source unless they take the toothbrush out of their mouth, rotate the toothbrush, and look at the status of the light source. Thus, the user may not brush for the recommended brushing time interval since they have to periodically check the status of the light source during the recommended brushing time interval. Another limitation of known toothbrushes is that as soon as the toothbrush is activated, a timer in the toothbrush starts counting the time over the recommended brushing time interval. Since, the known toothbrushes do not take into account the time required to apply toothpaste to the toothbrush, the user may not brush for the recommended brushing time interval if they activate the toothbrush prior to applying the toothpaste to the toothbrush.

U.S. Pat. No. 6,606,755 issued to Robinson et al. describes a toothbrush having a light source for signaling when a recommended brushing time interval has started and ended. In particular, the toothbrush includes a handle portion having a translucent portion configured to allow the transmission of light therefrom around substantially the entire circumference of the toothbrush. The toothbrush further includes a tip portion attached to the handle portion having a plurality of bristles extending therefrom. The tip portion is detachable from the handle portion. The toothbrush further includes a light emitting diode disposed within the handle portion proximate to the translucent portion. Finally, the toothbrush includes a control circuit disposed within the handle portion electrically connected to the light emitting diode.

U.S. Pat. No. 5,544,382 issued to Giuliani et al. describes a vibrating toothbrush, which includes a handle member, an elongated arm which has a brush-head at the distal end thereof, and a drive assembly for moving the brush-head at a selected velocity. Responsive to an on/off switch on the toothbrush is an on/off variable, which enables a master clock to produce a drive signal, the on/off variable being reset by a 120-second timer. A quadtimer variable, when in the enabled state, is responsive to the on/off switch to produce an audible signal and a difference in brush velocity at 30-second intervals within the 120-second period.

U.S. Pat. No. 5,930,858 issued to Jung describes an electric toothbrush which includes a timing circuit to signal to a user the expiration of a first period (T1) corresponding to an optimum brushing time. An On/Off switching device is provided which is controllable by the timing circuit and by means of which the electric toothbrush can be turned on and off. The timing circuit controls the On/Off switching of a go0 device such that following expiration of the first period (T1) the electric toothbrush is turned on and off repeatedly within a second period (T2). As a result, the user of the electric toothbrush "senses" directly the end of the first period (T1), that is, the end of the optimum brushing time, from the variation in the operating mode of the electric toothbrush.

U.S. Patent Application Number 20080060154 published to Jansheski describes an illuminated toothbrush that includes a one-piece body of molded plastic construction having a handle portion and a head portion, bristles extending outwardly from the head portion of the body, one or more sources of visible light located on within the head portion of the body and configured to direct visible light toward the bristles to illuminate locations being brushed during use of the toothbrush, and a circuit contained within the body configured to be activated by a user after use of the toothbrush. When activated, the circuit operates to illuminate the illumination sources for a predetermined period of time corresponding to a desired brushing interval and then turn the illumination sources off.

U.S. Pat. No. 7,409,741 issued to Dworzan describes a toothbrush provided with a head containing bristles, a neck and a handle. An eccentrically rotational weight is engaged for rotation with a motor, the weight disposed within the head. The motor is disposed within the handle. The head and neck are integrally formed with a natural resonance frequency of vibration approximately equal to the rotational speed of the motor and synchronized therewith.

U.S. Pat. No. 6,202,242 issued to Salmon et al. describes a light emitting electric toothbrush and method of use by children, comprised of a robust high-strength, plastic construction, and which toothbrush employs both light and vibration to assist in the development of suitable dental hygiene skills.

U.S. Patent Application Number 20060262516 published to Dowling et al. describes methods and systems for illuminating a variety of household products and other items using color-controlled illumination systems that include lights under the control of processors.

SUMMARY OF THE INVENTION

The present invention divides a person's teeth into quadrants and allocates a time for brushing their teeth split into four timed intervals corresponding to a person's upper right and left sides, and lower right and left sides of their teeth. Using the invention a person quickly learns to allocate the appropriate amount of time to brush the different parts of their mouth. In addition, the invention provides a novel way to make teeth brushing a pleasant and interesting experience for all age ranges including young children in the process of establishing a regular teeth brushing routine.

The present invention is a battery powered toothbrush made up of a head with bristles, a neck and a handle. A battery powered motor is disposed within the handle. An eccentrically rotational weight is engaged for rotation by the motor. The inventive toothbrush includes a neck portion and a handle portion, both portions having a translucent portion configured to allow the transmission of light therefrom around substantially the entire circumference of the toothbrush. The toothbrush houses an electrical circuit, which includes a processor and at least two LEDs (light emitting diodes), at least one of which internally lights up the neck and optionally also the head and the ends of the bristles attached to the head. At least two of the LEDs in the circuit are capable of emitting different colored light with respect to each other. The at least two LEDs are switched on for a predetermined time in a predetermined sequence under the control of the processor. In one embodiment of the invention a first LED housing contains first and second LEDs either of which upon activation internally illuminates the neck of the toothbrush to provide illumination along and from the entire length of the neck of the toothbrush. The handle, neck and head each have a different intensity of vibration of sufficient extent to be noticeable to a child. The intensity of vibration increases in magnitude from the handle to the head, wherein the head has the highest intensity of vibration, the neck less than the head, and the handle less than the neck.

A method for controlling a light source disposed in a translucent region of a toothbrush for indicating when a recommended brushing time interval has started and ended is provided. The inventive method includes the steps of alternatively switching the light source to emit first and second colors after predetermined time intervals. The recommended brushing time comprises the sum of four predetermined time intervals.

A toothbrush and method in accordance with the present invention represents a significant improvement over conventional toothbrushes and methods. In particular, the inventive toothbrush utilizes at least one translucent portion and a light source disposed therein to emit light 360° around the circumference of the toothbrush. Accordingly, a user can easily see when the recommended brushing time interval has elapsed without having to periodically take the toothbrush out of their mouth to check the status of the light source.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
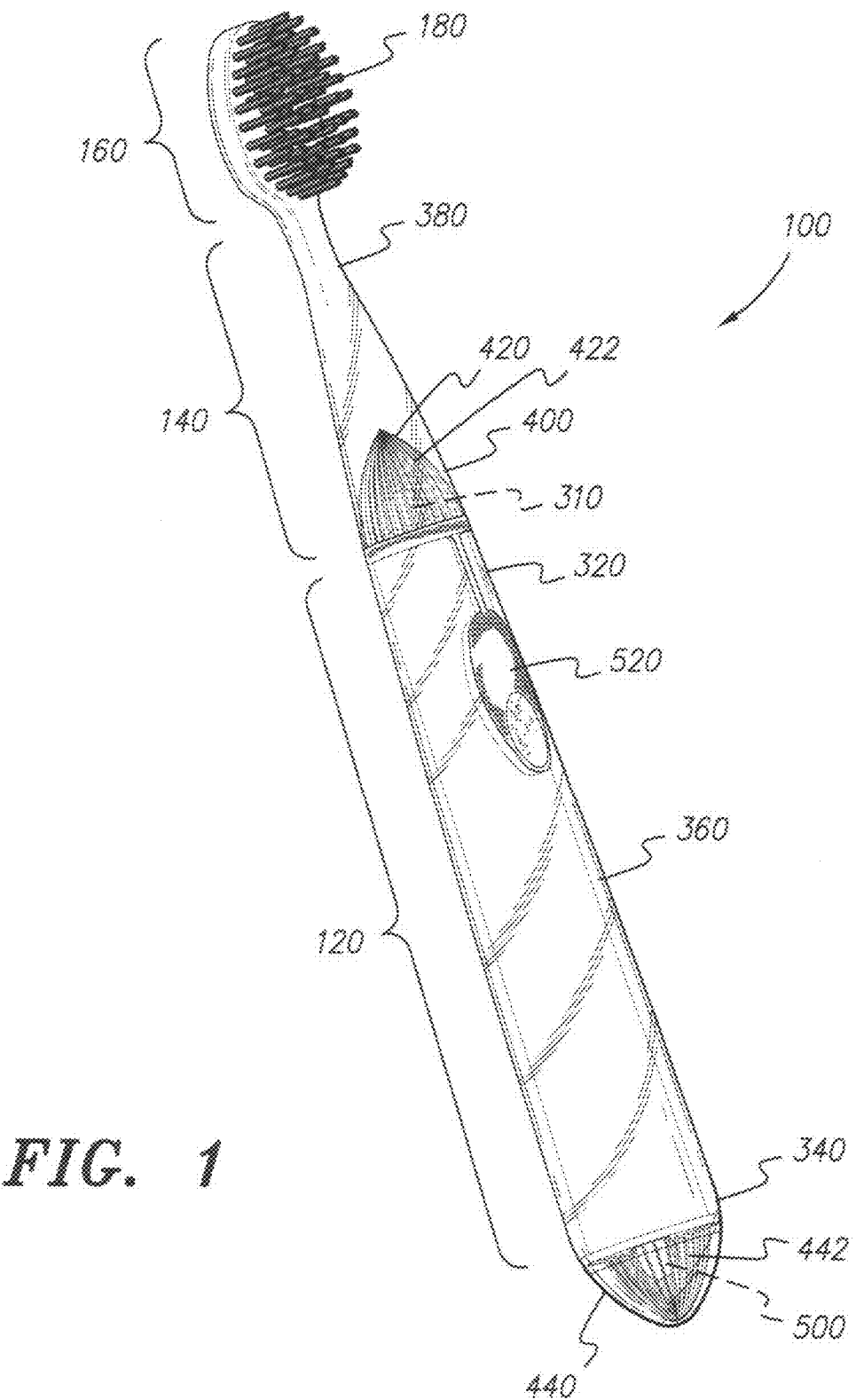
FIG. 1 shows a perspective view of a toothbrush according to the invention.
Figure 2:
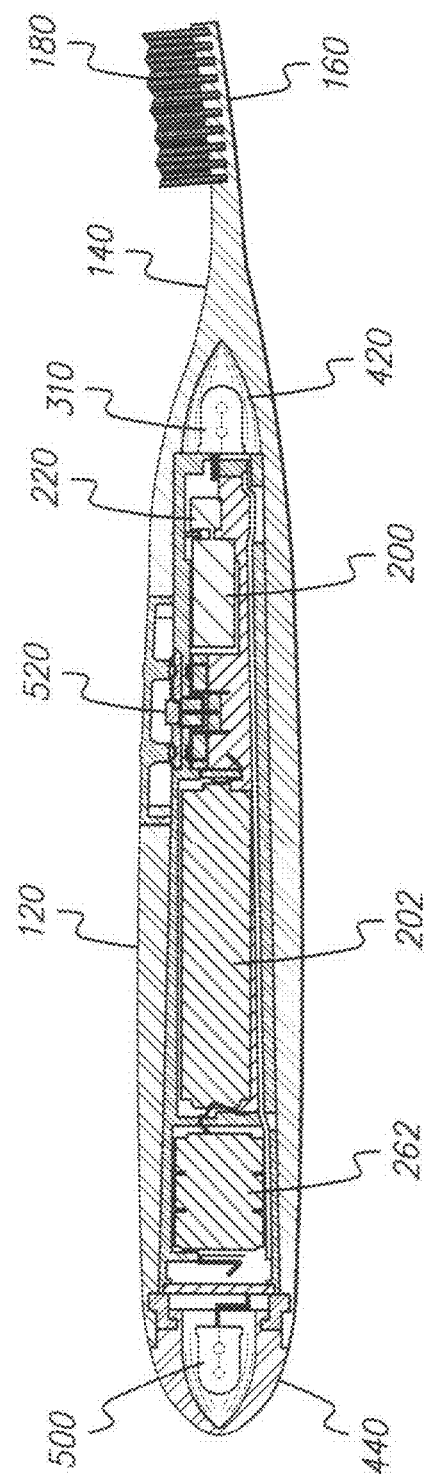
FIG. 2 shows a sectional view of the toothbrush of FIG. 1.

The present invention is directed to hand held appliances, and more especially hand held electrically powered toothbrushes. The toothbrush of the invention is denoted by the reference numeral 100 as a whole. It should be noted that whenever a child's teeth are referenced in this paper, the same applies to a healthy adult's mouth and teeth therein.

FIG. 1 shows a perspective view of the toothbrush 100. The toothbrush 100 includes handle 120 designed to allow a user to grasp toothbrush 100, a neck 140 constructed of a translucent or transparent material such as polypropylene or other similar materials, and a head 160 with bristles 180 extending there-from. The handle 120 defines opposite ends with a middle section there-between. Specifically, the handle 120 defines upper handle end 320, lower handle end 340, and middle handle portion 360 located between opposite handle ends 320 and 340. The handle 120 can be made out of any suitable material such as opaque plastic or transparent or translucent plastic or a combination thereof, but since there is no requirement for the LEDs of the invention to be located in the handle 120 the handle 120 can be made out of opaque plastic. The neck 140 and head 160 can be manufactured as a single integral piece and subsequently attached to the upper handle end 320. Thus, head 160 may also be translucent or transparent like neck 140 to allow for transmission of light therefrom.

The neck 140 defines an upper neck end 380, and a lower neck end 400. A first LED housing 420 extends from the upper handle end 320 into the interior of lower neck end 380. First and second LEDs 280 and 300 (shown in more detail in FIG. 4) are located inside first LED housing 420. The first LED housing 420 and lower neck end 400 are sufficiently transparent to allow a user to see the light emitted from the first and second LEDs 280 and 300 through the transparent or translucent material forming neck 140 and head 160. The lower neck end 400 is of sufficient interior diameter to accommodate the first LED housing 420, and is affixed to the upper handle end 320. It should be understood that any suitable light source can be used in place of each LED mentioned in this application, although LEDs are preferred.

Figure 3:
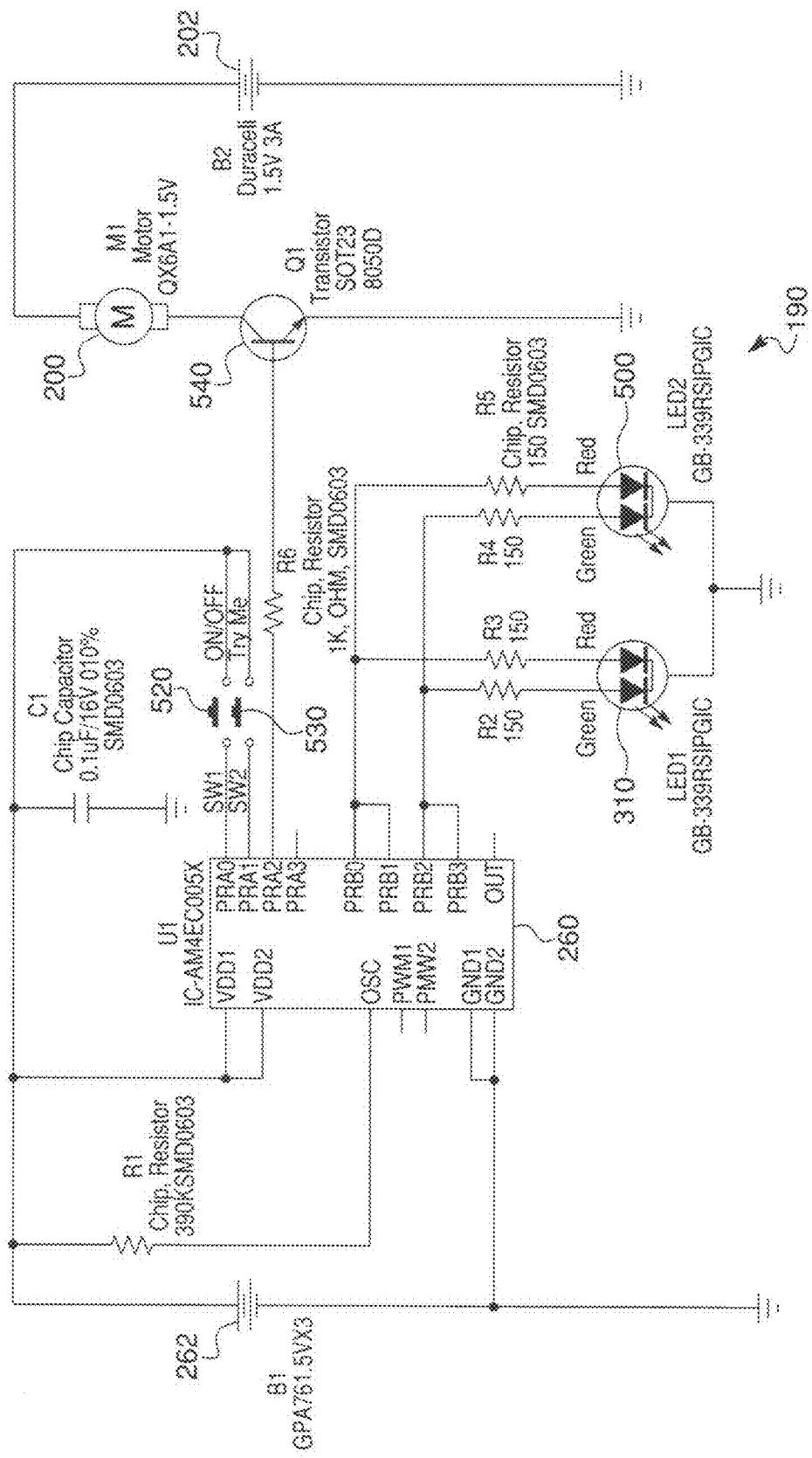
FIG. 3 shows a circuit schematic according to the invention.

Referring to FIG. 1, LED housing 420 is provided to emit light from toothbrush 100 to visually signal when a recommended brushing time interval has started and ended. The first and second LEDs 280 and 300 respectively emit a first colored light during one time interval and a second colored light for a second time interval, both intervals being for predetermined periods of time in a predetermined sequence. The first colored light and the second colored light can be any color such as, but not limited to, blue and yellow respectively and vice versa, but it is preferred that the first colored light is green and the second colored light is red. However, the first and second LEDs 280 and 300 can emit any color so long as the colors they emit are eminently distinguishable from each other with respect to a healthy human eye so as to easily discern the end of one time interval and the beginning of another. The first and second LEDs 280 and 300 can be provided as a dual-LED, and more specifically as a first dual diode 310 (see FIGS. 3 and 4). In the circuit schematic of FIG. 3 the first dual LED 310 is provided in the form of a GB-339 LED series dual diode. It is preferred that the first and second colors produced by first and second LEDs 280 and 300 respectively match the third and fourth colors produced by a third LED 460 and a fourth LED 480 which make up a second dual LED 500 (see FIGS. 3 and 4).

Figure 4:
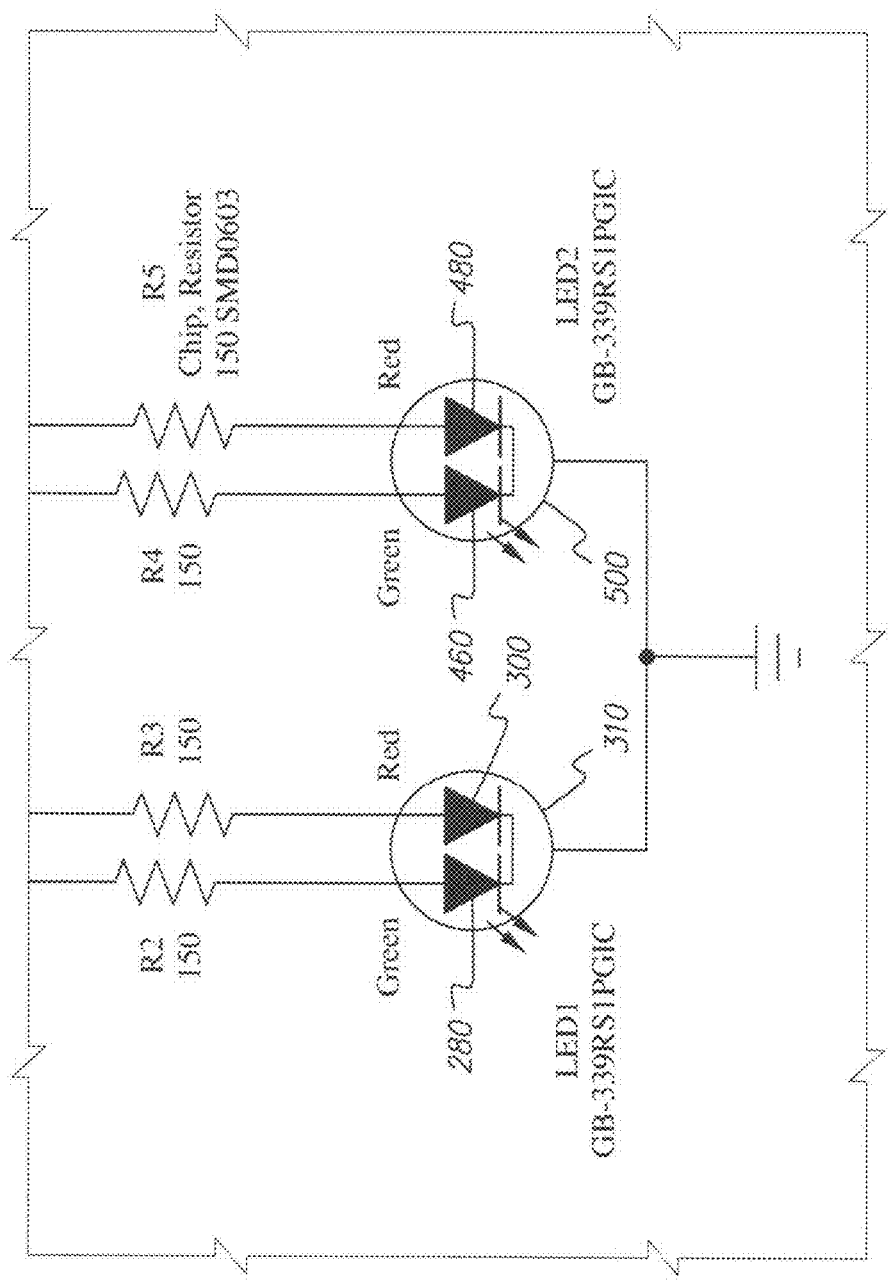
FIG. 4 shows an enlarged partial view of the circuit schematic of FIG. 3.

Still referring to FIG. 1, a second LED housing 440 is shown attached to the lower handle end 340. Third and fourth LEDs 460 and 480 (shown in FIG. 4) are positioned inside the second LED housing 440. The second LED housing 440 is sufficiently transparent to allow a user to see the light emitted by the third and fourth LEDs 460 and 480. The third and fourth LEDs 460 and 480 emit a third colored light and a fourth colored light, respectively. The third colored light is preferably red and the fourth colored light is preferably green. However, the third and fourth LEDs 460 and 480 can emit any color so long as the colors they emit are eminently distinguishable from each other with respect to a healthy human eye. The third and fourth LEDs 460 and 480 can be provided as a dual-LED. As shown in FIG. 4 the third and fourth LEDs 460 and 480 make up the second dual LED 500. In the circuit schematic of FIG. 3 the second dual LED 500 is provided in the form of a GB-339 LED series dual diode, but any suitable dual LED can be used. It is preferred that the third and fourth colors produced by third and fourth LEDs 460 and 480 respectively match the first and second colors produced by the first and second LEDs 280 and 300 which form part of the first dual LED 310 (see FIG. 4).

As noted previously, the neck 140 and/or head 160 can be made of transparent or translucent plastic. Each LED upon activation is visible around the entire circumference of the toothbrush 100. In addition, upon separate activation, the first and second LEDs 280 and 300, respectively, emit first and second colored light to illuminate the inside of neck 140 and if the head is made of transparent or translucent plastic then the inside of head 160. The end portions of bristles 180 in contact with head 160 are also illuminated. Thus, regardless of how a user or child holds handle 120, light is seen emanating from neck 140 and optionally head 160. This lighting effect produced in the neck 140, and optionally the head 160, will likely serve to fascinate children.

In a preferred embodiment the first and third LEDs 280 and 460, respectively located inside first and second LED housings 420 and 440, are switched on simultaneously under the control of processor 260. The first and third LEDs 280 and 460 respectively provide first and third colored light from first and second LED housings 440 and 460 for a first ¼ T time interval then lapse, then second and fourth LEDs 300 and 480 simultaneously provide second and fourth colored light for a second ¼ T time interval respectively from first and second LED housings 440 and 460 then lapse, then first and third LEDs 280 and 460 simultaneously provide first and third colored light for a third ¼ T time interval respectively from first and second LED housings 440 and 460 and lapse, and finally second and fourth LEDs 300 and 480 simultaneously provide second and fourth colored light for a fourth ¼ T time interval respectively from first and second LED housings 440 and 460 then lapse. Since the first and second LEDs 280 and 300 are located at one end of the handle 120, and the third and fourth LEDs 460 and 480 are located at the other end of handle 120 it follows that light is emitted through 360° from each end of the handle 120 in ¼ T segments of time under the control of the processor 260, wherein the LEDs 280, 300, 460 and 480 can be powered any suitable battery such as, but not limited to, a second battery 262 via processor 260 (see circuit schematic shown in FIG. 3). In addition, light from the first LED housing 420 illuminates the interior of neck 140 and some of this light diffuses into the head 160 and may illuminate the ends of the bristles 180 in contact with head 160.

The handle 120, neck 140 and head 160 each have a different intensity of vibration. The intensity of vibration increases in magnitude from the handle to the head. More specifically, during normal operation of the toothbrush 100 the motor and weight produce a first, second and third intensities of vibration in the handle 120, neck 140 and head 160, respectively. The intensity of vibration increasing from the first to the third intensity of vibration wherein a user such as a child would notice that the head 160 vibrates more than the neck 140; and the neck 140 vibrates more than the handle 120. It is expected that the novel changes in intensity of vibration between the handle 120, neck 140 and head 160 will serve to excite a child's curiosity and establish a regular pattern of teeth-brushing.

In a preferred embodiment the first and second LEDs 280 and 300, and the third and fourth LEDs 460 and 480 respectively emit first, second, third and fourth colored light for predetermined periods of time in a predetermined sequence under the control of the processor 260. While the LEDs can be any suitable color, it is preferred that the first and third LEDs 280 and 460 are green, and the second and fourth LEDs 300 and 480 are red.

The first 420 and second 440 LED housings can be made out of any suitable material such as transparent or translucent plastic. The first 420 and second 440 LED housings may respectively include a first plurality of striations 422 and a second plurality of striations 442 as shown in FIG. 1. The first plurality of striations 422 help direct light up into the neck 140 with some light diffusing into head 160 of toothbrush 100. Alternatively the first 420 and second 440 LED housings can optionally take the form of plastic Fresnel lenses. For example, the first LED housing 420 can be provided in the form of a Fresnel lens to direct light from the first and second LEDs into and up the neck 140 and thence partly into head 160 to produce a lighting effect that is likely to pique the interest of a child making for a pleasurable teeth brushing experience. The handle 120, neck 140, and head 160 (and bristles 180 attached to the head 160) can also be made out of any suitable material. For example, the handle 120, neck 140 and head 160 can be made out of a polymer such as plastic. The bristles 180 may be made of nylon or other conventional toothbrush bristle material. Upon assembly the handle 120, neck 140 and head 160 may form one integral piece.

In one embodiment of the invention the head 160 is made of translucent or transparent plastic such as, but not limited to, translucent polypropylene, wherein the neck 140 is at least partially hollow to accommodate the first LED housing 420 and the neck 140 is made of a transparent or translucent plastic such as, but not limited to, polypropylene. The neck 140 tapers inward from the lower neck end 400 to the upper neck end 380 (see FIG. 1). It has been surprisingly found that this combination achieves a vividly exciting lighting effect when either of the first and second LEDs 280 and 300 located in first LED housing 420 are switched on by processor 260. The first and second LEDs 280 and 300 individually transmit light up inside the neck 140 to provide child-pleasing illumination from and along the entire length of the neck 140 from the lower neck end 400 to the upper neck end 380. Some of the light from the LEDs 280 and/or 300 may diffuse into the head 160 from the upper neck end 380 to light up the ends of the bristles 180 connected to the heat 160. This lighting effect along and from the neck 140 and optionally into the head 160 of toothbrush 100 is believed to be hitherto unknown.

The toothbrush 100 includes an electrical circuit 190 therein. An example of a suitable electric circuit 190 is shown in schematic form in FIG. 3. The electrical circuit 190 includes motor 200, a first battery 202 (to power motor 200), a second battery 262 (to power processor 260 and first and second dual diodes 310 and 500, respectively), a user operable first switch 520, an optional user operable second switch 530, and a transistor 540 in series with motor 200. The first and second dual diodes 310 and 500 are shown in FIG. 1 attached to the upper handle end 320 and lower handle end 340, respectively. Either or both of the batteries 202 and 262 can be replaceable or rechargeable batteries. It is preferred that the batteries 202 and 262 are not replaced or recharged, but are provided with sufficient charge to power the toothbrush 100 through two brushings per day for between one and four months, and preferably between 2 and 3 months. It is preferred that the batteries 202 and 262 last about 3 months and upon their discharge the toothbrush 100 is thrown away taking care to comply with relevant laws and guidance on battery disposal. The processor 260 can be any known microprocessor that either includes memory or is operably linked to memory. The memory may include random access memory (RAM), read only memory (ROM), or erasable programmable ROM (EPROM).

When the first switch 520 is closed the processor 260 runs the first and second LEDs 280 and 300, and the third and fourth LEDs 460 and 480 through a predetermined lighting sequence corresponding to four quarters of a user's teeth; the first switch 520 also causes the processor 260 to send a small current out via output "PRA2" to switch on transistor 540 and allow the motor 200 to work for T time interval (which causes rotation of eccentric weight 220 for T time interval).

In the preferred embodiment closing first switch 520 acts as a signal for the processor 260 to switch on the transistor 540 for T time interval, during which the first and third LEDs 280 and 460 are switched on simultaneously for a first ¼ T time interval and lapse under the control of the processor 260, followed by the second and fourth LEDs 300 and 480 switched on simultaneously for a second ¼ T time interval and lapse under the control of the processor 260, followed by first and third LEDs 280 and 460 are switched on simultaneously for a third ¼ T time interval and lapse under the control of the processor 260, and finally the second and fourth LEDs 300 and 480 are switched on simultaneously a fourth ¼ T time interval and lapse. Thus while the LEDs 280, 300, 460 and 480 are switched on in a predetermined sequence under the control of processor 260 the motor 200 is also switched on via transistor 540 also under the control of processor 260. T can be any suitable predetermined time interval; for example, T can be any numeric value between 1 minute and 4 minutes, 1.5 minutes and 3 minutes, 1.75 minutes and 2.5 minutes). A preferred value for T is 120 seconds to provide four time periods corresponding to the four quarters of a user's teeth: LEDs 280 and 460 green (30 s) followed by LEDs 300 and 480 red (30 s) followed by LEDs 280 and 460 green (30 s) followed by LEDs 300 and 480 red (30 s). As the LEDs change color after each of four ¼ T time intervals this acts as a visual signal to the user to position the toothbrush in the next un-brushed quadrant of their mouth.

When either of the first and third LEDs 280 and 460 respectively emit first and third colored light to illuminate the inside of neck 140 and optionally the inside of head 160 and the end portions of bristles 180 in contact with head 160 are also illuminated. Thus, regardless of how a user or child holds handle 120, light is seen emanating from neck 140 and optionally head 160.

The optional second switch 530 causes the processor 260 to run the LEDs through a test sequence without switching on transistor 540. For example, closing the optional second switch 530 acts as a signal for the processor 260 to cause the first and third LEDs 280 and 460 to switch on simultaneously for a first ½ S time interval and lapse under the control of the processor 260, and second and fourth LEDs 300 and 480 to switch on simultaneously for a second ½ S time interval, wherein S can have any suitable predetermined value between 5 and 60 seconds, and preferably between 10 and 30 seconds.

In the alternative, the optional second switch 530 causes the processor 260 to run the LEDs through a test sequence and switches on transistor 540 to drive motor 200 and thence eccentric weight 220 causing the handle 120, neck 140 and head 160 (with bristles 180 with ends attached thereto) to vibrate. In the alternative example, closing the optional second switch 530 acts as a signal for the processor 260 to switch on transistor 540 for S time interval and cause the first and third LEDs 280 and 460 to switch on simultaneously for a first ½ S time interval and lapse under the control of the processor 260, and second and fourth LEDs 300 and 480 to switch on simultaneously for a second ½ S time interval, wherein S can have any suitable predetermined value between 5 and 60 seconds, and preferably between 10 and 30 seconds.

In one embodiment, the handle 120, neck 140 and head 160 respectively have first, second and third resonance frequencies of vibration. In this embodiment the third resonance frequency of vibration is greater than the second resonance frequency of vibration, which in turn is greater than the first resonance frequency of vibration such that the frequency of vibration increases in ascending order from the handle 120 to the neck 140 to the head 160 of toothbrush 100. The bristles 180 having substantially the same frequency of vibration as the head 120 to which the bristles 180 are connected.

In another embodiment, the handle 120, neck 140 and head 160 each have a resonance frequency of vibration approximately equal to the rotational speed of the motor 200, but the amplitude of vibration varies between the handle, neck and head. Specifically, the handle 120, neck 140 and head 160 respectively have first, second and third amplitudes of vibration. In this embodiment the third amplitude of vibration is greater than the second amplitude of vibration, which in turn is greater than the first amplitude of vibration such that the amplitude of vibration increases in ascending order from the handle 120 to the neck 140 to the head 160 of toothbrush 100.

In one embodiment the electrical circuit 190 includes just two LEDs such as first and second LEDs 280 and 300. At least two of the LEDs emit different colored light with respect to each other. The at least two LEDs are switched on for a predetermined time in a predetermined sequence under the control of the processor 260. For example, the processor 260 includes memory on which is stored an algorithm which upon activation ensures a first LED emits light of a first color for ¼T seconds followed by a second LED that emits light of a second color for ¼ T followed by the first LED emitting light of the first color for ¼ T seconds followed finally by the second LED that emits light of the second color for a final time period of ¼T seconds, where T=any suitable time period such as, but not limited to, 120 s (120 seconds, i.e., two minutes such that ¼ T seconds is 30 seconds); T can be, for example, any numeric value between 1 minute and 4 minutes, 1.5 minutes and 3 minutes, 1.75 minutes and 2.5 minutes). The first and second colors can be any color such as green and red, respectively. In this example, a first LED 280 shines green for 30 seconds followed by the second LED 300 shining red for 30 seconds followed by the first LED 280 shining green a second time for 30 seconds followed by the second LED 300 shining red a second time for 30 seconds, wherein each 30 s (thirty second) period indicates to the user when to brush a further quarter of their mouth with the toothbrush 100. That is, each color represents one quarter of a person's mouth where a person (user) brushes a first quarter of their teeth during the first green period (represented by the first LED shining green for 30 seconds) then a second quarter of the user's teeth (represented by the second LED 300 shining red for 30 seconds) then a third quarter of the user's mouth (represented by the first LED 280 shining green for 30 seconds) then a fourth quarter of the user's mouth (represented by the second LED 300 shining red for 30 seconds), where "teeth" in this context means teeth in a user's mouth. In this non-limiting example there are four periods corresponding to the four quarters of a user's teeth: LED 280 green for 30 s→LED 300 red for 30 s→LED 280 green for 30 s→LED 300 red for 30 s.

It should be understood that the electric toothbrush and the various elements described herein are set forth merely to facilitate a complete understanding of the toothbrush device 100, and should not be read as limiting the invention to toothbrush applications.

What is claimed is:

1. A toothbrush, comprising:
   a handle portion having opposed first and second ends, said handle portion designed to allow a user to grasp said toothbrush when the toothbrush is in a teeth-cleaning operating mode;
   a head portion that is at least partially transparent or translucent and that contains bristles;
   a neck portion that is at least partially transparent or translucent position between the first end of said handle portion and said head portion;
   a first housing that is at least partially transparent or translucent extending from the first end of the handle portion and into the neck portion;
   a first light source disposed within said first housing;
   a control circuit disposed within said handle portion configured to control said first light source to interactively switch said first light source from a first color to a second color for a first predetermined time interval and a second predetermined time interval, respectively;
   a second housing that is at least partially transparent or translucent extending from the second end of the handle portion;
   a second light source disposed within said second housing; and
   said control circuit configured to control said second light source to interactively switch said second light source from a first color to a second color for a first predetermined time interval and a second predetermined time interval, respectively.

2. The toothbrush of claim 1 wherein said control circuit is configured to control said second light source for switching said second light source to a third color different from said second color for a third predetermined time interval, and said control circuit switches said second light source to a fourth color different from said third color for a fourth predetermined time interval.

3. The toothbrush of claim 2 wherein said first and third colors of said second light source are the same and the second and fourth colors of said second light source are the same.

4. The toothbrush of claim 1 wherein said second light sources comprises two light emitting diodes.

5. The toothbrush of claim 1 wherein said translucent portion of said neck portion is illuminated when said first light source is switched on by said control circuit.

6. The toothbrush of claim 1 wherein said translucent portion is configured around substantially an entire circumference of said toothbrush.

7. The toothbrush of claim 1 wherein each of said time intervals is equal to ¼×T wherein T is equal to between 1 and 4 minutes.

8. The toothbrush to claim 1 including a battery powered motor disposed within said handle portion, said motor including an eccentrically rotational weight to cause vibrations of said bristles.

9. A toothbrush, comprising:
   a handle portion having opposed first and second ends designed to allow a user to grasp said toothbrush when the toothbrush is in a teeth-cleaning operating mode, a head portion that is at least partially transparent or translucent and that contains bristles, and a neck portion that is at least partially transparent or translucent and that is positioned between the first end of said handle portion and said head portion; a first housing that is at least partially transparent or translucent extending from the first end of the handle portion and into the neck portion; a first light source disposed within said first housing; and, a control circuit disposed within said handle portion configured to control said first light source to interactively switch said first light source from a first color to a second color for a first predetermined time interval and a second predetermined time interval, respectively;
   said control circuit is further configured to control said first light source for switching said first light source to a third color different from said second color for a third predetermined time interval, and said control circuit switches said first light source to a fourth color different from said third color for a fourth predetermined time interval;
   a second housing that is at least partially transparent or translucent extending from the second end of the handle portion;
   a second light source disposed within said second housing;
   said control circuit configured to control said second light source to interactively switch said second light source from a first color to a second color for a first predetermined time interval and a second predetermined time interval, respectively; and
   said control circuit is further configured to control said second light source for switching said second light source to a third color different from said second color for a third predetermined time interval, and said control circuit switches said second light source to a fourth color different from said third color for a fourth predetermined time interval.

10. The toothbrush of claim 9 wherein said first and third colors of said first or second light sources are the same and the second and fourth colors of said first and second light sources are the same.

11. The toothbrush of claim 9 wherein each of said first and second light sources comprises two light emitting diodes.

12. The toothbrush of claim 9 wherein said translucent neck portion is configured around substantially an entire circumference of said toothbrush.

13. The toothbrush of claim 9 including a battery powered motor designed with said handle portion, said motor including an eccentrically rotational weight to cause vibrations of said bristles.

14. The toothbrush of claim 1 comprising vibration means for vibrating the head portion, the neck portion and the handle portion, wherein the intensity of vibration of the neck portion is greater than the intensity of vibration of the handle portion.

* * * * *